United States Patent [19]

Ashby

[11] Patent Number: 5,092,892

[45] Date of Patent: Mar. 3, 1992

[54] INTRAMEDULLARY CENTRALIZER

[75] Inventor: Alan M. Ashby, Maidenhead, England

[73] Assignee: Howmedica International Inc., Shannon, Ireland

[21] Appl. No.: 601,554

[22] Filed: Oct. 23, 1990

[51] Int. Cl.⁵ .............................................. A61F 2/28
[52] U.S. Cl. ....................................... 623/16; 606/95
[58] Field of Search ............... 623/16, 18, 23; 606/95

[56] References Cited

U.S. PATENT DOCUMENTS

| | | | |
|---|---|---|---|
| 3,793,650 | 2/1974 | Ling et al. | 683/18 |
| 4,302,855 | 12/1981 | Swanson | 606/95 |
| 4,523,587 | 6/1985 | Frey | 606/95 |
| 4,753,657 | 6/1988 | Lee et al. | 623/23 |

FOREIGN PATENT DOCUMENTS

| | | | |
|---|---|---|---|
| 0006408 | 1/1980 | European Pat. Off. | |
| 0179626 | 4/1986 | European Pat. Off. | 623/18 |
| 0187093 | 7/1986 | European Pat. Off. | 623/23 |
| 0220427 | 5/1987 | European Pat. Off. | |
| 1409053 | 10/1975 | United Kingdom | |
| 2052267 | 1/1981 | United Kingdom | 606/95 |
| 2104391 | 12/1984 | United Kingdom | |

OTHER PUBLICATIONS

Whiteside, Leo A., Amador, David and Russell, Kenneth, "The Effects of the Collar on Total Hip Femoral Component Subsidence", Jun. 1988, Clinical Orthopaedics and Related Research, pp. 120–126.
Pamphlet for Whiteside Total Hip System (Dow Corning Wright).
Pamphlet for Exeter Universal Hip System (Howmedica).

Primary Examiner—David J. Isabella
Attorney, Agent, or Firm—Peter C. Richardson; Lawrence C. Akers; Raymond W. Augustin

[57] ABSTRACT

A centralizer for the stem of a prosthetic orthopedic implant adapted for implantation into a medullary canal has a hollow annular body portion. The annular body portion has an interior for receiving the stem of the implant. The body portion also includes at least three spring elements extending outwardly from the exterior surface of the body portion. Each spring element has a portion thereof extending generally tangentially with respect to the axial extent of the tapered stem and deformable circumferentially and inwardly towards the stem upon insertion into the medullary canal.

14 Claims, 2 Drawing Sheets

INTRAMEDULLARY CENTRALIZER

BACKGROUND OF THE INVENTION

This invention relates to a centralizer for the stem of an intramedullary prosthesis such as a femoral implant. More particularly it relates to a centralizer with deformable tangentially extending spring elements in the form of wings or fins.

Centralizers for example, as shown in British Patent Application 2 104 391 are used to centralize the distal stem in the femoral canal. A disadvantage with devices of the type shown in U.K. 2 104 391 is that the resilient elements which are provided to centralize the tip end of the stem of the prosthesis can only be pressed inwardly to a certain extent and difficulties can arise if the intramedullary canal is particularly narrow. Another centralizing device using vertically extending elements is shown in U.S. Pat. No. 3,793,650 which issued to the inventors of U.K. patent application 2 104 391. A polyethylene sleeve is shown in the Exeter Universal hip system similar to that of 3,793,650 in that the spring elements extend vertically. It will be appreciated that these spacers are not only intended to centralize the distal tip of the prosthesis but also to prevent it from actually engaging a wall of the canal.

A further disadvantage with the prior art devices is that, when used in cemented applications, they tend to leave voids and air bubbles in the cement behind them as they are pushed downwardly and these voids and air bubbles also form behind the fingers, that is, between the fingers and the body of the device. This is to be avoided as it can become a point of weakness and crack initiation within the cement mantel.

Polymethylmethacrylate sleeves are known and have been taught by Leo A. Whiteside et al in an article published in June 1988 entitled "The Effects of the Collar on Total Hip Femoral Component Subsidence" and sold as the "Whiteside Total Hip System". However, this device is merely a cylindrical sleeve which can only centralize the distal stem in a precisely reamed canal.

Also, it is advantageous to provide a centralizer on which in certain circumstances the forces causing subsidence, such as a heavy load on the prosthesis, are high enough to cause the stem to move further into the cement mantle and thus further into the centralizer, which offers the advantage of being able to absorb this movement by providing means to accept the movement and cover the end of the stem to thus prevent it piercing further into the cement and causing cracking.

The centralizer of the present invention overcomes the problems set forth above. According to the present invention, a centralizer for the stem of a prosthesis for introduction into an intramedullary canal comprises an annular body portion for location on the distal tip of the stem of a prosthetic component. The body portion is provided with three or more resiliently deformable spring elements in the form of fins or wings projecting outwardly from the centralizer body portion which are adapted to fold circumferentially and inwardly towards the body portion.

Thus, with this construction the fins are deflected inwardly towards the body portion as the stem enters the narrower part of a canal. In addition, due to the fact that the fins can be made of relatively thin sections, they cut their way through the bone cement as the stem is introduced into the canal without having to bulldoze their way through the cement leaving voids in their wake. Thus, voids and air bubbles are prevented or reduced.

A further advantage of the centralizer of the present invention is that its thin fins or wings can collapse inwardly down to a diameter of less than 10 mm and therefore the surgeon will less frequently be faced with the need to trim parts or all of the fins or wings off the body portion. This extra step has sometimes been necessary with constructions as set forth in the U.K. Patent Application 2 104 391 referred to above.

Preferably the fins or wings extend outwardly from the body portion in tangential directions so that they are lined up ready for deformation in the correct direction. The body portion can be provided with control elements to allow the distal tip of the implant to move further into the centralizer after fitting and after the prosthesis and centralizer have been cemented into place. With this arrangement, the body portion is preferably shaped to enclose the tip end of the prosthesis stem.

SUMMARY OF THE INVENTION

It is an object of the present invention to provide a centralizer for the stem of an orthopedic implant which can be inserted into a medullary cavity filled with bone cement without creating voids therein.

It is a further object of the present invention in which the centralizer has deformable spring element which extends generally tangentially to the axis of the stem and which can deform radially inwardly towards said stem.

These and other related objects are achieved by a centralizer having a body portion in the form of a cup, one end of which is closed and the other having a control element provided by a deformable control collar which can be at a midpoint or at the open end of the cup. Thus, the tip end is always enclosed, even after some subsidence of the prosthesis has taken place, without the tip distorting as resistance to this subsidence.

Alternatively, the centralizer can be provided in combination with a separate enclosure for housing the distal tip of the stem, which enclosure is provided with the control element for allowing the tip to move further into said enclosure after fitting.

The enclosure can be provided in the form of a cup portion, one end of which is closed, and the control element may be in the form of a collar at a mid-point or at the other end of a cup.

The centralizer and/or the enclosure means can be made from a material similar to bone cement material (polymethylmethacrylate) which will thus enable it to become well integrated with the cement mantle and avoid any weakening or discontinuity creation. Thus, it can be made from polymethylmethacrylate to which a plasticizer has been added to provide more flexibility. Such plasticizers may be di-2-ethylhexyl phthalate or butyl benzyl phthalate. Alternately, the centralizer may be made of n-butyl methacrylate homopolymer which is inherently more flexible. The bone cement will creep so that after becoming integrated with the centralizer the control means can continue to function.

The invention also includes centralizer and/or enclosure means as set forth above in combination with a prosthetic device, for example the stem of a hip or knee replacement prosthesis.

These and other objects and advantages of the present invention will become apparent from the following description of the accompanying drawings, which disclose several embodiments of the invention. It is to be understood that the drawings are to be used for the purpose of illustration only, and not as a definition of the invention.

BRIEF DESCRIPTION OF THE DRAWINGS

The invention can be performed in various ways and some embodiments will now be described by way of example and with reference to the accompanying drawings wherein similar reference elements refer to similar elements throughout the several views, wherein.

DESCRIPTION OF THE PREFERRED EMBODIMENTS

Figure 1:
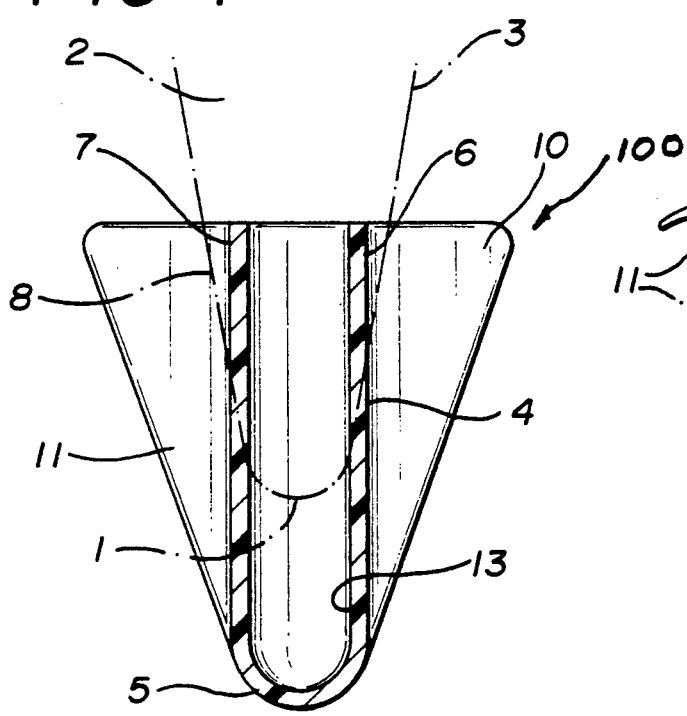
FIG. 1 is a cross-sectional side elevation of a centralizer according to the present invention.

As shown in FIG. 1, the preferred centralizer 100 comprises elements for centralizing a prosthesis and at the same time includes elements for accommodating subsequent subsidence of the stem of the prosthesis into a polymerized, cured or set cement mantle in a medullary canal after surgical implantation.

The device acts to locate the distal tip 1 of the stem 2 of a prosthetic hip device indicated in phantom by broken lines 3 by locating it within the medullary canal in which it is fitted to prevent contact between the stem of the hip or knee device and the bone and to act to accommodate the subsidence referred to.

Centralizer 100 comprises a body portion 4 in the form of a cup having a lower closed end 5 and an upper open end 6. Upper end 6 of body 4 is provided with an expandable control collar 7. In FIG. 1 collar 7 is shown in the unengaged position, but when pushed onto a prosthesis it will tend to deform outwardly to the position shown by broken lines 8.

Three equally spaced tangentially projecting spring elements 10, 11, 12 are provided for holding the tip 1 of stem 2 away from the wall of a medullary canal. Of course, more than three spring elements may be utilized. The dimensions of control collar 7 are arranged so that when the centralizer is pushed onto the tip of the prosthesis it deforms slightly into the position shown by broken lines 8, where it is held in position. The prosthesis is now fitted by pushing it into the medullary canal which has been suitably prepared and which contains the necessary bone cement. Because the cement has not yet polymerized, cured or set, the forces are not sufficient to force the collar 7 all the way up stem tip 1. As the prosthesis is inserted into the appropriate canal position, elements 10, 11, 12 deform inwardly to ensure that there is the correct central location. A typical deformed position of the arms is shown in phantom in FIG. 2. The central collar 7 acts as a seal around the stem 1 to prevent entry of bone cement and is effective to maintain a small void distal to the stem tip.

In the arrangement described, the preferred centralizer is molded from polymethylmethacrylate to which a plasticizer or modifier has been added to provide more flexibility and so that spring elements 10, 11, 12 are resiliently deformable as is the control collar 7. Such a plasticizer may be DEHP (di-2 ethylhexyl phthalate), butyl benzyl phthalate or SBS (styrene butodiene styrene) block copolymer. With the preferred centralizer in position, the polymethylmethacrylate centralizer becomes well integrated with the bone cement which can be of similar material without the plasticizer, thus avoiding any weakening of the cement mantle or void creation.

When the prosthesis has been in use for some time, it may have a tendency to subside, i.e. sink further into the cement. This can be accommodated by the control collar deforming to allow the prosthesis to pass further into cup-shaped body 4. It will be appreciated that this will considerably reduce the chances of the elements 10, 11, 12 breaking away from body 4 or of the body 4 itself sinking further. The movement is merely accommodated by deformation of the body/collar and the surrounding cement mantle. Moreover, the tip of the prosthesis remains completely covered, the gap between the lower end of the prosthesis and the inner surface 13 of the lower end of the cup thus accommodating the subsidence movement.

A device of this kind -can be used with any stem, provided the inner dimensions of the cup are large enough and of suitable geometry to fit the end of the hip or knee stem. The device however, is particularly appropriate for use with prostheses such as the "EXETER" hip prosthesis which has no calcar collar at its proximal end. This type of prosthesis stem is designed with the principle of taper engagement between the metal stem and the cement. It is important that this taper can re-engage if there is any movement in the cement and, in order to achieve this, it is important that there be no cement around the distal tip of the stem.

Figure 3:
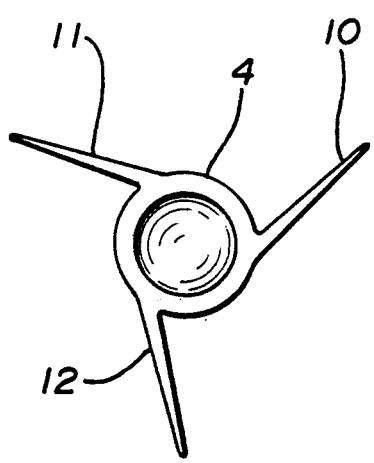
FIG. 3 is a plan view of an alternative construction.

FIG. 3 shows an alternative construction in which similar reference numerals are used to indicate similar parts. In this construction, however the spring elements in the form of fins or wings 10, 11, 12 are straight rather than curved although they are still tangential to the cup 4. Once again, as is the preferred embodiment, a body with three fins or wings is shown, but it will be appreciated that four or five wings could be used if desired.

Figure 4:
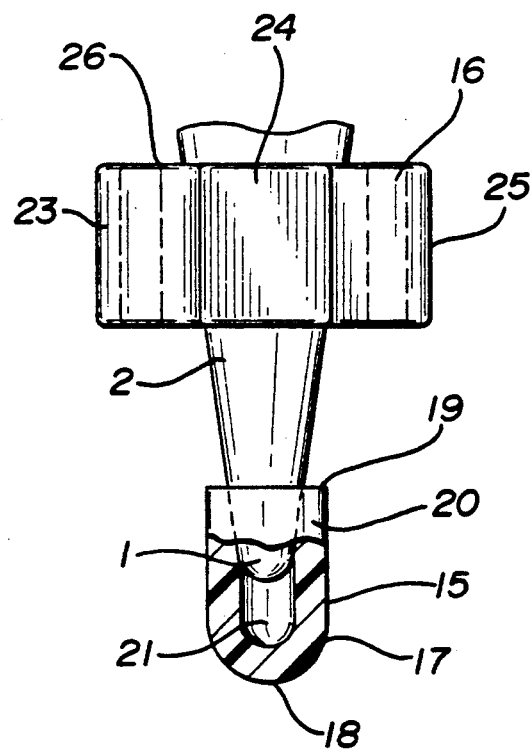
FIG. 4 is a side view partly in section of an alternative construction of a centralizer mounted in combination with enclosure means on the stem of an intramedullary prosthesis.
Figure 5:
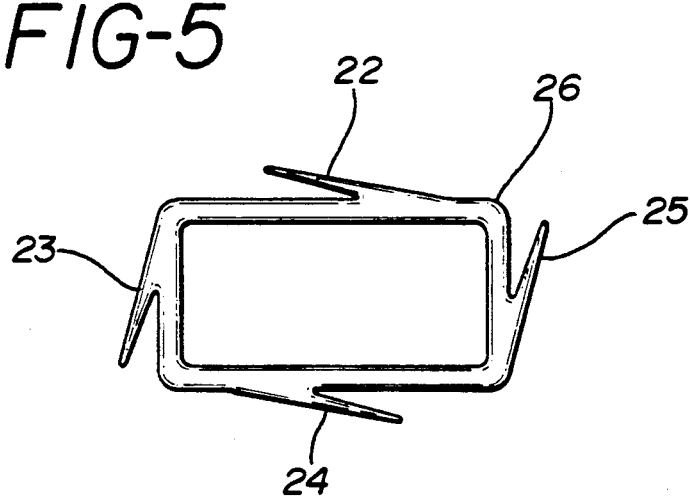
FIG. 5 is a plan view of the centralizer shown in FIG. 4.

In the arrangement shown in FIGS. 4 and 5 separate enclosure element 15 is provided and which is separate from the centralizer 16 and, as above with the preferred embodiment, is attached to the stem tip prior to insertion. The stem of the prosthesis is indicated by reference numeral 2 and its tip by reference numeral 1.

The enclosure element 15 is in the form of a cup portion 17 having a lower closed end 18 and an upper open end 19. The upper end 19 of the cup portion is provided with a deformable collar 20 similar to collar 7 of the preferred embodiment. The inner surface of the lower end of the cup 17 is indicated by reference numeral 21.

Figure 2:
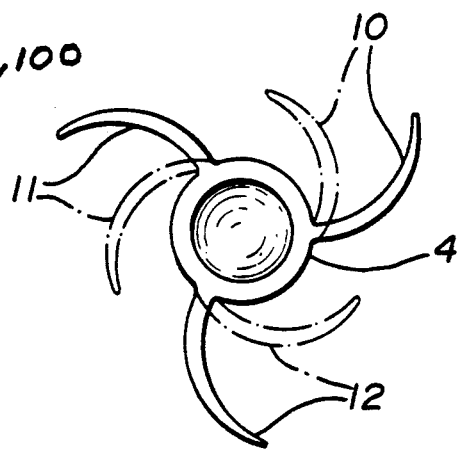
FIG. 2 is a plan view of the centralizer shown in FIG. 1.

The centralizer 16 can, for example, have a plan view similar to FIGS. 2 and 3, but in the arrangement shown comprises four equally spaced arms 22, 23, 24 and 25 which extend tangentially from a ring or wall 26. This ring acts as a control element to locate the centralizer on the prosthesis. The centralizer and enclosure element 15 can again be molded from polymethylmethacrylate to which a plasticizer as described above has been added to provide more flexibility so that the arms 22, 23, 24, 25 are resiliently deformable as is the ring 26. The dimensions of the collar are chosen so that when the centralizer is pushed onto the tip of the prosthesis the ring expands slightly so that it is resiliently held in position. The cup 18 is then pushed onto tip 1 of the prosthesis with control collar 20 deforming to hold cup 18 in position. The prosthesis is now implanted in the manner described above with the same process with regard to the cement and prosthesis subsidence occurring as set forth and as described with regard to the preferred embodiment of FIGS. 1, 2 and 3.

In the arrangements described above, the deformable control collar 7 is provided on the body 4 at its open upper end 6 and the body has substantially parallel sides. With the shown cylindrical internal geometry of body 4, very narrow stems might bottom out in the centralizer, and with the thickest stems the centralizer may fall off the stem prior to insertion during surgery.

Figure 6:
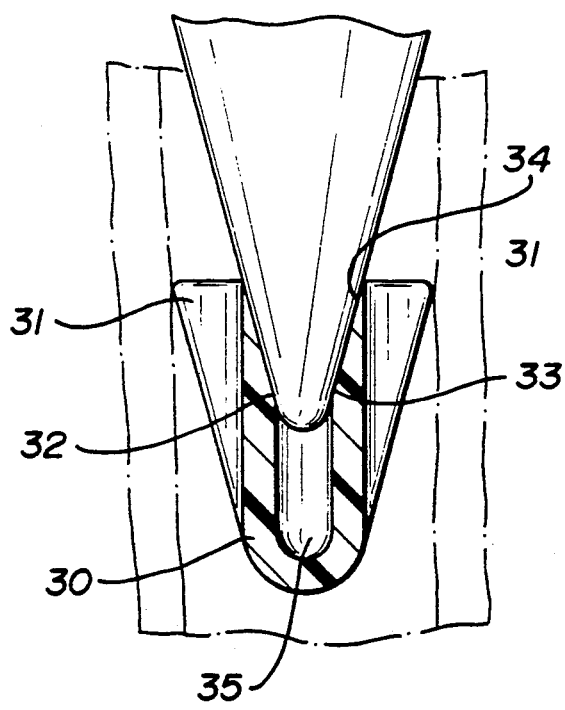
FIG. 6 is another alternative embodiment of the centralizer of the present invention.
Figure 7:
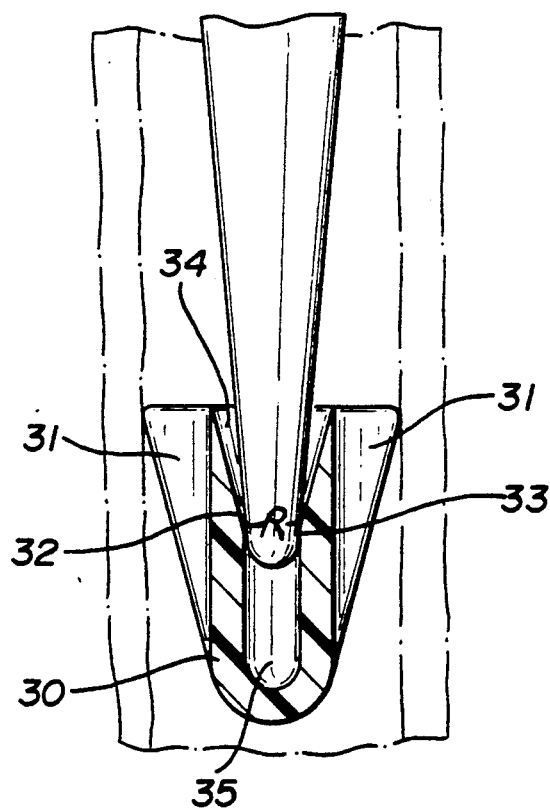
FIG. 7 is the centralizer of FIG. 6 shown attached to a stem of smaller cross-section.

FIGS. 6 and 7 show an alternative construction which is more adaptable to stems of widely varying shapes and sizes. In this embodiment the centralizer comprises a cup-shaped body portion 30 with three or more tangentially projecting arms indicated by reference numeral 31. The upper portion of the inside surface of the cup is tapered as shown at 32 so that an effective control collar 33 of a smaller diameter than the inner diameter at the open end of body 30 is provided at a point displaced from the upper end 34.

In the arrangement shown in FIG. 7, which is for a narrow stem size, the reference letter R indicates radius of the stem tip. The dimensions are predetermined so that the radius of the cylindrical bore 35 of the cup is the same as the radius of the tip of the distal stem.

By making the open upper end of the bore tapered from point 32 to open end 34 in the manner described, it has been found that a single centralizer size can fit several sizes of stem. Thus, FIG. 6 shows the use of a centralizer for a large stem size and FIG. 7 illustrates the use of the same centralizer for use with a narrow stem size. In each case it will be seen that the cylindrical portion of the internal base of bore 35 adjacent point 32 provides the control collar which couples centralizer 100 to stem 2 and provides for subsidence into the central bore of the centralizer.

It will be appreciated that the same type of internal configuration and dimensions for the centralizer body can be employed with the separate enclosure tip 15 of the kind shown in FIG. 4. The centralizer 16 in FIG. 4 and FIG. 5 can have a straight sided internal bore or it could be tapered from one end to the other or again, alternatively, it could have reversed tapers or a taper at one end and be of substantially constant cross-section at the other. As is seen from FIG. 5, the cross-section of the internal bore can be dimensioned in accordance with the stem with which it is to be used, for example, it can be substantially rectangular, triangular, circular or any other suitable shape.

It will be appreciated that due to the material which is used, the parts become completely integrated with the cement, thus avoiding any discontinuity, weakening or void creation, but the inward movement of the prosthesis can be accommodated. The use of inwardly folding spring elements in the form of fins or wings allows the prosthesis to be used in narrow canals but more particularly is advantageous in as much as that when the prosthesis is inserted into the cement, the production of voids, gaps and holes behind the fins or wings is eliminated.

While several examples of the present invention have been described, it is obvious that many changes and modifications may be made thereunto, without departing from the spirit and scope of the invention.

I claim:

1. A prosthetic bone joint device for implantation into a medullary canal comprising:
    a component having a tapered intramedullary stem extending therefrom, said stem having a proximal end and a distal tip;
    a spacer having a hollow annular body portion with an interior generally conforming to the circumferential shape of said tapered intramedullary stem; and
    at least three spring elements extending outwardly from an exterior surface of said annular body portion, said spring members having a portion thereof extending generally tangentially with respect to the axial extent of said tapered stem and deformable circumferentially and inwardly towards said stem upon insertion into the medullary canal.

2. The prosthetic device as set forth in claim 1 wherein said body portion has a cup-shape with a closed distal end and an open proximal end with the proximal end thereof having a predetermined diameter corresponding to a diameter of said tapered stem proximal of said distal tip of said stem.

3. The prosthetic device as set forth in claim 2 wherein said proximal end of said body portion is in the form of an expandable collar of predetermined axial length.

4. The prosthetic device as set forth in claim 2 wherein said body portion and spring elements are made from a deformable material.

5. The prosthetic device as set forth in claim 4 wherein said deformable material is polymethylmethacrylate with a plasticizer added thereto.

6. The prosthetic device as set forth in claim 2 wherein the interior of said cup-shaped body portion has a portion at the distal end thereof having a first diameter therein and a tapered portion tapering outwardly from said distal end portion to a larger diameter at the proximal end of said cup-shaped body portion.

7. A centralizer for the tapered stem of a prosthetic orthopedic implant adapted for implantation into a medullary canal, said centralizer comprising:
    a hollow annular body portion having an interior for receiving the stem of the implant; and
    at least three spring elements extending outwardly form an exterior surface of said annular body portion, said spring members having a portion thereof extending generally tangentially with respect to the axial extent of said tapered stem and deformable circumferentially and inwardly towards said stem upon insertion into the medullary canal.

8. The centralizer as set forth in claim 7 wherein said body portion has a cup-shape with a closed distal end and an open proximal end with the proximal end thereof having a predetermined diameter corresponding to a diameter of said tapered stem proximal of said distal tip thereof.

9. The centralizer as set forth in claim 8 wherein said cup-shaped body portion has a generally cylindrical interior.

10. The centralizer as set forth in claim 8 wherein said proximal end of said body portion is in the form of an expandable collar of predetermined axial length.

11. The centralizer as set forth in claim 8 wherein said body portion and spring elements are made from a deformable material.

12. The centralizer as set forth in claim 11 wherein said deformable material is a polymethylmethacrylate with a plasticizer added thereto.

13. The centralizer as set forth in claim 8 wherein the interior of said cup-shaped body portion has a portion at the distal end thereof having a first diameter therein and a tapered portion tapering outwardly from said first diameter at said portion at the distal end to a larger diameter at the open the proximal end of said cup-shaped body portion.

14. The centralizer as set forth in claim 13 wherein said portion at the distal end of said body portion has a deformable control collar adjacent the first diameter of said tapered portion.

* * * * *